United States Patent [19]

McIntyre et al.

[11] Patent Number: 5,334,153
[45] Date of Patent: Aug. 2, 1994

[54] CATHETER PURGE APPARATUS AND METHOD OF USE

[75] Inventors: Jon T. McIntyre, Lowell, Mass.; James F. Crittenden, Hollis, N.H.

[73] Assignee: C. R. Bard, Inc., Murray Hill, N.J.

[21] Appl. No.: 957,725

[22] Filed: Oct. 7, 1992

[51] Int. Cl.⁵ ............................................. A61M 25/00
[52] U.S. Cl. .......................................... 604/99; 604/96; 604/280; 606/194
[58] Field of Search ............... 604/96, 97, 99, 101, 604/163, 164, 171, 256, 280; 606/192, 194

[56] References Cited

U.S. PATENT DOCUMENTS

| | | |
|---|---|---|
| 4,000,739 | 1/1977 | Stevens . |
| 4,029,099 | 6/1977 | Fifield . |
| 4,062,363 | 12/1977 | Bonner . |
| 4,205,675 | 6/1980 | Vaillancourt . |
| 4,327,723 | 5/1982 | Frankhouser . |
| 4,327,735 | 5/1982 | Hampson . |
| 4,362,150 | 12/1982 | Lombardi, Jr. et al. ............ 604/99 |
| 4,424,833 | 1/1984 | Spector et al. . |
| 4,430,081 | 2/1984 | Timmermans . |
| 4,483,340 | 11/1984 | Fogarty et al. ............ 604/194 |
| 4,551,137 | 11/1985 | Osborne . |
| 4,564,014 | 1/1986 | Fogarty et al. ............ 604/194 |
| 4,582,181 | 4/1986 | Samson . |
| 4,613,329 | 9/1986 | Bodicky ............ 604/163 |
| 4,634,433 | 1/1987 | Osborne . |
| 4,638,805 | 1/1987 | Powell . |
| 4,657,536 | 4/1987 | Dorman . |
| 4,684,363 | 8/1987 | Ari et al. . |
| 4,692,200 | 9/1987 | Powell . |
| 4,696,304 | 9/1987 | Chin ............ 604/97 |
| 4,714,461 | 12/1987 | Gabel . |
| 4,715,378 | 12/1987 | Pope et al. . |
| 4,726,374 | 2/1988 | Bales et al. . |
| 4,748,982 | 6/1988 | Horzewski et al. . |
| 4,759,751 | 7/1988 | Gabel et al. . |
| 4,767,409 | 8/1988 | Brooks . |
| 4,793,351 | 12/1988 | Landman et al. . |
| 4,811,737 | 3/1989 | Rydell et al. . |
| 4,821,722 | 4/1989 | Miller et al. . |
| 4,844,092 | 7/1989 | Rydell et al. . |
| 4,846,174 | 7/1989 | Willard et al. ............ 604/96 |
| 4,917,094 | 4/1990 | Lynch et al. . |
| 4,930,341 | 6/1990 | Eutemeuer . |
| 4,983,167 | 1/1991 | Sabota . |
| 5,114,408 | 5/1992 | Fleischhaker et al. . |
| 5,149,326 | 9/1992 | Woodgrift et al. . |

FOREIGN PATENT DOCUMENTS 0366478  5/1990  European Pat. Off. ............ 604/96

Primary Examiner—John D. Yasko
Assistant Examiner—Anthony Gutowski
Attorney, Agent, or Firm—Darby & Darby

[57] ABSTRACT

A balloon catheter having a mechanism for purging air therefrom having a flexible inflation shaft coaxially disposed over a less flexible inner shaft, and a fitting attached to the proximal end of the inflation shaft and slidably mounted on the inner shaft. The fitting contains a variable high pressure seal and a passive low pressure seal. The fitting may be slid along the inner shaft towards its distal end to collapse the inflation shaft in an accordion manner, thereby reducing the volume that would be occupied by air in the inflation shaft and the balloon. The remaining air is removed with a syringe that may be attached to the fitting. In a second embodiment disclosed, the balloon may be collapsed in an accordion manner along with the inflation shaft, further reducing the volume that would be occupied by air. The low pressure seal of the fitting prevents air from entering the catheter during the purging operation.

40 Claims, 2 Drawing Sheets

CATHETER PURGE APPARATUS AND METHOD OF USE

FIELD OF INVENTION

This invention relates in general, to balloon catheters adapted for introduction into passageways and organs of the body, and in particular, to balloon dilation catheters with an air purging feature and their method of use.

BACKGROUND OF THE INVENTION

Transluminal angioplasty, using balloon catheters, has become increasingly popular because it is significantly less traumatic than the open heart surgery required for a coronary bypass operation. In the angioplasty procedure, an elongated catheter having a dilatation balloon or expander member at its distal end is routed through the vascular system to a coronary artery that may be partially occluded with fatty deposits or other types of lesions. Once placed in the desired position, the balloon of the catheter is expanded by a liquid under relatively high pressure to compress the fatty deposit against the walls of the vessel, and force open the occluded artery.

During this procedure, there is a possibility that the balloon may burst or the catheter tube may fail under the relatively high pressure of the inflation liquid. Therefore, the inflation liquid must be carefully selected to avoid catastrophic injury to the patient should such bursting or failure occur, and the liquid is accidentally released into the vessel of the body.

Air and other gases, if present in the catheter, are not quickly absorbed by the blood and are particularly dangerous, with the possibility that an air embolus might be formed. Moreover, if the balloon is inflated with a radiopaque marking fluid, the presence of air may result in error in the accurate positioning of the balloon relative to the occlusion being treated.

Accordingly, it is necessary to purge the air from the catheter prior to use. In the initial stages of the procedure, upon removal of the balloon catheter from its package, these catheters are typically purged of air prior to use so that only the inflation liquid fills the catheter. In accordance with one method of preparing the balloon catheter for use in the body, the balloon and catheter lumen are filled with an inflation liquid, typically a saline solution mixed with radiographic contrast media. The air mixes with the liquid which is then withdrawn from the catheter. Unfortunately, this time consuming procedure must be repeated as many times as necessary to ensure the proper removal of air.

Another technique to purge air from a catheter utilizes catheters that provide a separate tube, which may be removable, that is connected to an opening in the balloon so that air can be forced out through it as the liquid fills the balloon. For an example of this type of catheter, see U.S. Pat. No. 4,684,363 to Ari et al. However, with this type of catheter, air may be reintroduced through the opening of the balloon when the liquid is withdrawn to collapse the balloon before insertion into the patient. The additional tube also creates disadvantages when it is desirable to provide a catheter having a very low profile.

It has also been the practice to purge air from a catheter by creating a vacuum inside the lumen of the catheter, typically in conjunction with a syringe used for liquid filling purposes. Trapped air is withdrawn from the catheter and replaced by the liquid medium which is injected into the lumen of the catheter by the syringe. In such a procedure, air which is purged from the catheter is collected in the syringe. Keeping the syringe in an upright position to permit the air to rise to the plunger of the syringe, the liquid medium is then injected into the catheter to provide inflation of the balloon.

This air purging technique still requires extra time, and involves a number of repeated steps and exercises. Moreover, there is a degree of difficulty in purging air from catheters of smaller sizes, or which have a construction which does not facilitate this air purging technique.

Both the amount of time required and the degree of difficulty in purging the air from a catheter prior to its use have been a problem in the field of angioplasty. The procedures described above are time consuming and require additional equipment to be located in the catheterization laboratory, which may already be crowded with instruments and devices.

Accordingly, there is a need for a balloon tipped catheter having an improved mechanism for purging air from the balloon and catheter lumen.

SUMMARY OF THE INVENTION

In view of the foregoing, it is an object of the present invention to provide a balloon dilatation catheter that includes a mechanism to facilitate the removal or purging of air prior to use of the catheter.

Another object is to provide an improved method of purging air from balloon dilatation catheters.

In a preferred embodiment, a dilatation catheter is provided having an elongate member; a flexible extendable elongate tubular member defining an inflation lumen therein, the flexible tubular member being disposed coaxially about the elongate member; a dilatation balloon in fluid communication with the flexible tubular member and being radially expandable to a preselected configuration in response to introduction of a fluid; and a modified Tuohy-Borst type fitting having a variable high pressure seal and a low pressure seal, connected to the proximal portion of the flexible tubular member and in fluid communication therewith, the fitting slidably mounted on the elongate member. To facilitate removal of air from the catheter, the Tuohy-Borst fitting may be slid along the elongate member towards its distal end to collapse the flexible tubular member in an accordion manner, thereby reducing the volume that would be occupied by air in the flexible tubular member. The remaining air may be removed with a syringe that is attached to the Tuohy-Borst fitting. The low pressure seal of the fitting prevents air from entering the catheter during the purging operation.

In an alternative embodiment, the dilatation balloon may be collapsed in an accordion manner along with the flexible tubular member, further reducing the volume that would be occupied by air.

A method is also provided for purging air from a dilatation catheter having an elongate tube defining an inflation lumen, comprising the steps of collapsing the elongate tube along its longitudinal axis to reduce the volume that would be occupied by air; providing a port in communication with the inflation lumen to allow air to escape; coupling a syringe having a plunger to the port; and retracting the plunger to withdraw any remaining air from the inflation lumen.

DETAILED DESCRIPTION OF A PREFERRED EMBODIMENT

The present invention contemplates an improved air purging mechanism for balloon tipped catheters that facilitates the removal of air from the balloon and the inflation lumen of the catheter.

Figure 1:
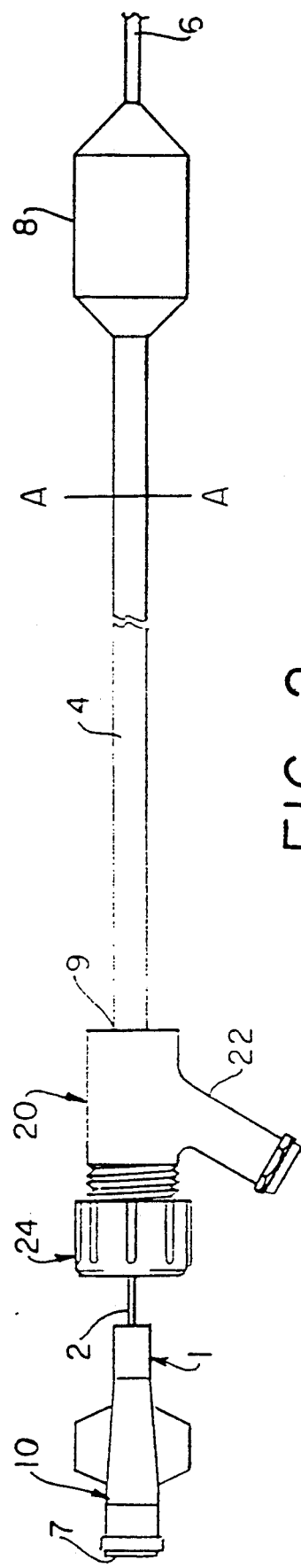
FIG. 1 is a side elevation view of a balloon catheter illustrating one embodiment of the air purging mechanism of the present invention in which the catheter is in a fully extended state.
Figure 2:
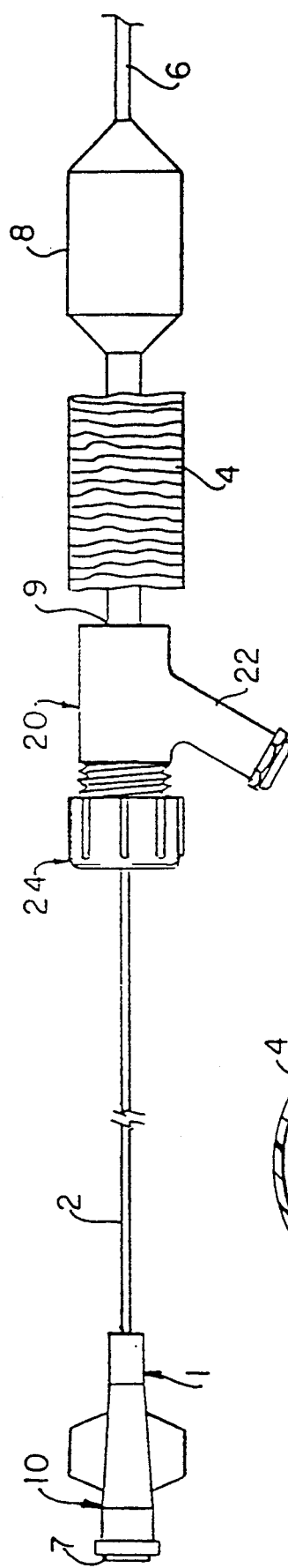
FIG. 2 is a side elevation view of a balloon catheter illustrating one embodiment of the air purging mechanism of the present invention in which the outer shaft of the catheter is in a collapsed, compressed state.
Figure 3:
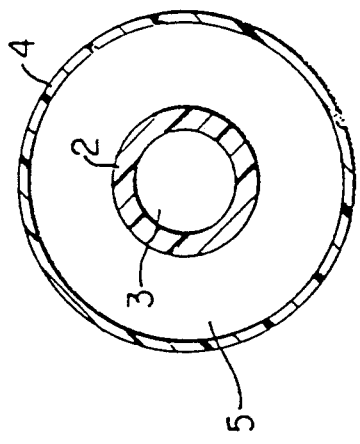
FIG. 3 is a sectional view taken on line A—A of FIG. 1.

Referring to the drawings, wherein like numerals refer to like components, there is illustrated in FIGS. 1-3 one embodiment of the present invention. In FIGS. 1-3, a balloon catheter 1 embodying the present invention is shown.

The balloon catheter 1 includes a fairly rigid, elongated, inner tubular member 2 which is provided with proximal and distal extremities 7 and 6, respectively, and which has a lumen 3 extending therethrough. The inner tubular member 2 may be formed of, for example, metal or any of several well-known suitable thermoplastic or thermo-set plastic materials.

The lumen 3, which may serve as a guidewire lumen, connects to a Luer-type fitting 10 mounted on the proximal extremity 7 of the inner tubular member 2 and is in communication therewith. It should be understood that although a Luer-type fitting 10 is preferred in the present invention, the invention is not so limited in that other available connective means may be used. Moreover, although the present invention preferably uses an inner tubular member 2 having a through lumen 3 for slidably receiving a guidewire therein, the use of a hollow tubular member is not critical to the invention. As is well known in the art, the present invention may be utilized with equal facility by having a fixed, solid core shaft or other suitable wire used in place of the inner tubular member 2, eliminating the need for an accompanying guidewire and the Luer-type fitting 10.

A flexible, thin film outer tubular member 4 (shown in its normal, fully extended state in FIG. 1, and bunched together or collapsed in FIG. 2) is coaxially disposed about the inner tubular member 2 and provides, in conjunction with the inner tubular member 2, an annular lumen 5 which extends longitudinally of the inner and outer tubular members 2 and 4.

The outer tubular member 4 is preferably formed of a suitable biaxially orientated thermo-plastic material, such as polyethylene terephthalate, which is commonly known by the acronym PET. The particular type of material used for the outer tubular member 4 is not critical to the invention, and other flexible materials suitable for accomplishing the same functions described above may also be used.

A modified fitting 20 of the well-known Tuohy-Borst type (hereinafter referred to as the "T-B fitting") is provided at a proximal end 9 of the outer tubular member 4 and slidably mounted on the inner tubular member 2. When loosened, the T-B fitting 20 is allowed to slide longitudinally along the inner tubular member 2. The T-B fitting 20 is sealingly connected to the proximal end 9 of the outer tubular member 4 forming a liquid-tight seal and a strong anchoring means for the outer tubular member 4.

The present invention provides for an expander member or balloon 8, as is commonly practiced in the art, located near the distal end of the catheter 1. The balloon 8, like the outer tubular member 4, also may be formed of a suitable thermo-plastic material such as PET or polyurethane, but it is not so limited. Preferably, the balloon 8 and outer tubular member 4 of the catheter 1 are made of a non-distensible material so that they can only be inflated to expand to a predetermined size. Further attempts to inflate such structures result in an increase in pressure, but no significant increase in diameter.

As may be appreciated by one skilled in the art, however, it would also clearly be possible in some applications to utilize an outer tubular member 4 and/or balloon member 8 made from an extendable, elastic material that in its normal state and configuration would be carried only at the distal end of the catheter 1. An elastic outer tubular member 4 and/or balloon member 8 could then be stretched or extended into the tightly drawn configuration illustrated in FIG. 1 by sliding the T-B fitting 20 towards the proximal end of the catheter 1.

The balloon 8 includes a necked down proximal extremity that extends longitudinally along the outer tubular member 4, and a necked down distal extremity that extends longitudinally along the distal end of the inner tubular member 2. The necked down proximal extremity of the balloon 8 tapers to a diameter which generally approaches that of the outer tubular member 4. Additionally, the necked down distal extremity of the balloon 8 tapers to a diameter which approaches that of the inner tubular member 2. The distal extremity of the balloon 8 and the inner tubular member 2 are bonded together so as to form a liquid-tight seal for the balloon 8 and the lumen 5.

It is preferable that the balloon 8 be integrally formed with the outer tubular member 4, such that the balloon 8 is an extension of the outer tubular member 4. However, the balloon 8 can be formed as a separate element which has its proximal extremity bonded to the outer tubular member 4, and its distal extremity secured to the distal extremity 6 of the inner tubular member 2. The proximal and distal extremities of the balloon 8 can be secured to form liquid-tight seals in a suitable manner such as by the use of an adhesive, or alternatively, by heat shrinking the same onto the outer tubular member 4 and inner tubular member 2 if the balloon 8 is formed of a heat shrinkable material.

As shown in the art, Radiopaque markers may optionally be provided in the form of radiopaque bands (not shown) which are secured to the inner tubular member 2 within the balloon 8 near the distal and proximal extremities of the balloon 8, or in the form of one band (not shown) in the center of the balloon 8. Suitable material such as gold, tungsten or platinum may be utilized for the bands.

In accordance with the present invention, the outer tubular member 4 may be disposed in an expanded, extended, or open formation (as shown in FIG. 1) for insertion and use into a body vessel. In this configuration, the T-B fitting 20 along with the proximal end 9 of the outer tubular member 4 sealingly attached thereto is positioned along the inner tubular member 2 as close as possible to the proximal end 7 of the catheter 1. The T-B fitting 20 is tightened about the inner tubular member 2 so that the outer tubular member 4 can be maintained in a tightly drawn, expanded condition.

Alternatively, the T-B fitting 20 may be loosened about the inner tubular member 2 to allow the outer tubular member 4 to be "bunched up" toward the distal end 6 of the catheter 1 (as shown in FIG. 2). In FIG. 2, the outer tubular member 4 is depicted in a collapsed or non-extended position. In this configuration, the outer tubular member 4 is contracted in an accordion-like fashion along its longitudinal axis into a series of tightly packed folds. To achieve this configuration, the T-B fitting 20 is loosened and, along with the outer tubular member 4 connected thereto, slid in a distal direction along the length of the inner tubular member 2, to be carried near the distal end 6 of the catheter 1.

Figure 5:
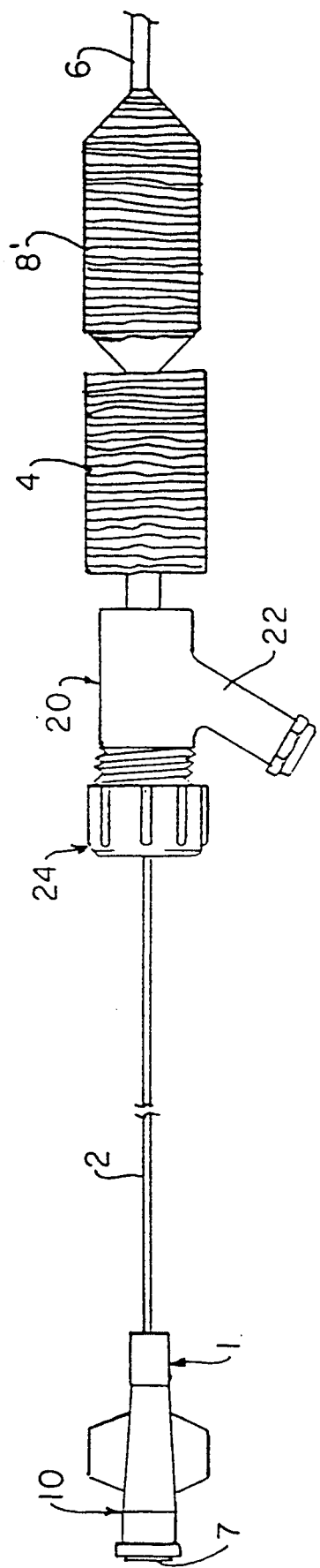
FIG. 5 is a side elevation of a balloon catheter illustrating an alternative embodiment of the air purging mechanism of the present invention in which the outer shaft of the catheter is and the dilatation balloon is in a collapsed, compressed state.

An additional embodiment of the present invention, shown in FIG. 5, provides for an expander member or balloon 8' also to be bunched-up or contracted in an accordion-like fashion along its longitudinal axis in addition to the outer tubular member 4 when the T-B fitting 20 is positioned as close as possible towards the distal end 6 of the catheter 1.

Referring to both embodiments of the invention, when the outer tubular member 4 is not in a collapsed or contracted state and is extended as much as can be permitted along the length of the inner tubular member 2, the lumen 5 serves as a balloon inflation lumen, providing a path for conducting pressurized fluids into and out of the expander member or balloon 8 for selective expansion and deflation thereof.

Figure 4:
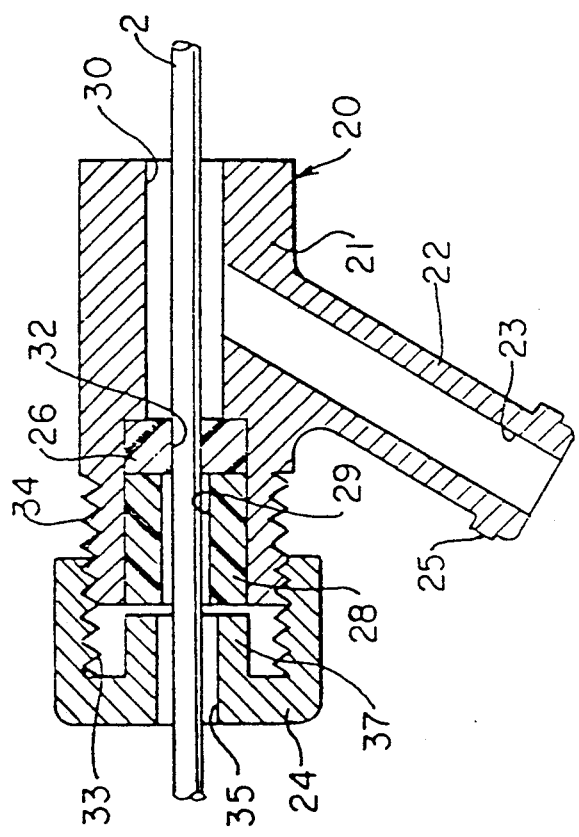
FIG. 4 is a cut away view taken along the longitudinal axis of a Tuohy-Borst type fitting provided in one embodiment of the present invention.

Referring now to FIG. 4, the T-B fitting 20 is shown in further detail. The T-B fitting 20 includes a housing 21 having a through lumen 30 extended along its longitudinal axis, in which the inner tubular member 2 is slidably disposed. The lumen 30 contains a tubular, resilient gasket 26 having an axial aperture 32 through which the inner tubular member 2 is received. The internal diameter of aperture 32 is about equal to the outer diameter of the inner tubular member 2, such that the gasket 26 provides a passive, low pressure sealing site for the inner tubular member 2 at the aperture 32. Advantageously, the gasket 26 provides an air-tight seal on the inner tubular member 2, while allowing movement of the gasket 26, and therefore the T-B fitting 20, along the length of the inner tubular member 2. As will be appreciated, the gasket may be made from a number of suitable materials such as rubber, latex or silicone, with a silicone gasket being preferred in the present invention.

A second tubular, resilient gasket 28, positioned adjacent to the proximal side of gasket 26 is provided in the space between the proximal end of lumen 30 and the proximal side of gasket 26. The second gasket 28 includes a lumen 29 that carries the inner tubular member 2 therethrough. The internal diameter of the lumen 29 is close in size to, but slightly greater than, the outer diameter of the inner tubular member 2. Like the first gasket 26, the second gasket 28 may also be formed of any suitable material, but will preferably be formed of silicone.

The proximal portion of the housing 21 contains an external thread 34 that is designed to be coupled to an end cap 24 containing an internal thread 33. The proximal portion of the housing 21 and the cap 24 are designed to be coupled together in an axial, telescoping, screw-threaded relation, such that relative rotation of the cap 24 to the housing 21 causes them to advance and retract relative to one another.

The cap 24 further includes a circular, centrally disposed hub 37 located in the center of the internal threads 33 of cap 24 that cooperates with the second gasket 28. The hub 37 is designed to extend partially within the space occupied by gasket 28 when the cap 24 is threaded onto the housing 21, thereby serving to seal the space between the cap 24 and the housing 21, and to compress the gasket 28 about the inner tubular member 2.

The cap 24 further includes a circular, axial opening 35, allowing the inner tubular member 2 to extend therethrough. The lumen defined by opening 35 is in axial alignment with lumen 30. Accordingly, the T-B fitting 20 of the present invention is designed so that the inner tubular member 2 can pass through the lumen 30, gaskets 26 and 28, the lumen 29, and the opening 35.

By using the T-B fitting 20, a variable pressure seal may be applied to the inner tubular member 2, depending upon the relative rotational adjustment of the cap 24 to the housing 21. As the cap 24 and the housing 21 are brought closer together, they compress the gasket 28 in a longitudinal manner. This, in turn, causes the lumen 29 of the gasket 28 to collapse inwardly, pressing against the portion of the inner tubular member 2 that occupies the lumen 29, thus providing a seal which presses against the inner tubular member 2 with a force that is dependent on the rotational position of the cap 24 and the housing 21.

The T-B fitting 20 may be loosened by rotating the cap 24 to allow it to slide along the inner tubular member 2 or alternatively it may be tightened to provide reliable, high pressure sealing against leakage of fluid when the balloon 8 and the lumen 5 are inflated. While the adjustable high pressure seal may be applied or released as desired, the low pressure seal provided by gasket 26 is constantly present to prevent leakage of air into the lumen 5 upon release of the high pressure seal.

As illustrated in FIG. 4, the housing 21 also includes a side leg 22 extending off of the housing 21 in a Y-shaped configuration. The side leg 22 further includes a through lumen 23 in communication with the lumen 30, and a fitting 25 containing an axial aperture, coupled to the distal end of the side leg 22. The fitting 25 is designed to receive a syringe or the like so that air may be purged from the lumen 5 and the balloon 8.

In a purging operation, the cap 24 of the T-B fitting 20 is rotated to release the high pressure seal applied to the inner tubular member 2. The T-B fitting 20 is then slid toward the distal end 6 of catheter 1. This causes the outer tubular member 4 to collapse and "bunch up" on the inner tubular member 2 towards the distal end 6 of the catheter 1 as shown in FIG. 2. By "bunching up" or contracting the outer tubular member 4, the available volume which air would occupy is greatly reduced, making it easier to remove the amount of air still present in the lumen 5. In the alternative embodiment which permits the balloon 8 to be collapsed or "bunched-up"

in addition to the outer tubular member 4, even more of the volume which air would occupy would be eliminated when the T-B fitting 20 is moved to the distal end 6 of the catheter 1.

With the outer tubular member 4 in its "bunched up" position toward the distal end of the catheter 1, a syringe (not shown) containing an amount of contrast fluid is connected to the side leg 22 of the T-B fitting 20. A vacuum is then created in the lumen 5 and balloon 8 by pulling back on the syringe plunger to draw air from the catheter into the syringe body.

The syringe containing a contrast medium and the withdrawn air is then held in a plunger-up position so that the air in the syringe body rises to the plunger of the syringe. Next, the T-B fitting 20 is slid proximally over the inner tubular member 2, thereby unfolding the accordion shape of outer tubular member 4. As the T-B fitting 20 is slid in a proximal direction, the contrast medium is drawn from the syringe into the lumen 5 and the balloon 8 of the catheter 1 to provide inflation thereof.

In lieu of manually sliding the T-B fitting 20 to the proximal end of the inner tubular member 2, the syringe may be used to fill the lumen 5 by depressing the plunger of the syringe, thereby using the pressure of the liquid to force the T-B fitting 20 back towards the proximal end of the inner tubular member 2. This latter procedure may be in some cases both faster and more free of air than the manual manipulation of the T-B fitting 20 in a proximal direction.

Once the T-B fitting 20 is positioned at the proximal end of the inner tubular member 2, the cap 24 of the T-B fitting 20 is threaded down such that the gasket 28 of the housing 21 is seated against and firmly held to the inner tubular member 2 to prevent movement of the T-B fitting 20.

Optionally, a three-way valve or stopcock (not shown) may be positioned between the syringe and the side leg 22. The valve may be set to an open position so that, as before, a vacuum may be created in the lumen 5 and balloon 8 by pulling back on the syringe plunger to draw air from the catheter into the syringe body.

After the air is drawn out of the catheter 1, the valve may be turned to a closed position so as to maintain the vacuum in the catheter by closing off the lumen 23 in the side leg 22. Next, the syringe is disconnected from the valve, and a separate inflation device (not shown) containing inflation fluid may be connected to the valve. Then, the valve may be set so that the inflation fluid in the inflation device will be in fluid communication with the lumen 23 of side leg 22 when the inflation device is connected to the valve. The lumen 5 and the balloon 8 of the catheter 1 may now be inflated by the inflation device instead of the syringe.

It is to be understood that the present invention may be used with equal facility and advantage in other non-dilatation catheter devices. Moreover, although the invention has been described in detail with particular reference to a preferred embodiment thereof, it should be understood that the invention is capable of other and different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

What is claimed:

1. A catheter comprising:
   a first tubular member having a distal portion, a proximal portion with a first fitting and having a lumen therein;
   a second tubular member having a distal portion and a proximal portion, and having a lumen therein, said second tubular member disposed coaxially about said first tubular member, said distal portion of said second tubular member being attached to said distal portion of said first tubular member so that said lumen of said second tubular member is fluid-tight;
   a second fitting connected to said proximal portion of said second tubular member in fluid communication therewith, said second fitting slidably mounted on said first tubular member;
   said second tubular member being flexible such that said second tubular member is adjustable in length along its longitudinal axis to allow said second fitting to be positioned along said proximal portion and said distal portion of said first tubular member.

2. A catheter according to claim 1, further comprising a balloon secured to said second tubular member, said balloon in fluid communication with said second tubular member and radially expandable to a configuration in response to the fluid.

3. A catheter according to claim 1, wherein said second fitting is a Luer fitting connected to said proximal portion of said first tubular member and in communication with said lumen of said first tubular member for receiving a guidewire therein.

4. A catheter according to claim 1, wherein said first tubular member is comprised of a rigid material.

5. A catheter according to claim 1, wherein said second tubular member is comprised of a flexible thin-filmed membrane that may be collapsed in an accordion manner along its longitudinal axis.

6. A catheter according to claim 2, wherein said balloon and said second tubular member are comprised of a flexible thin-filmed membrane that may be collapsed in an accordion manner along its longitudinal axis.

7. A catheter according to claim 1, wherein said second fitting further comprises a high-pressure seal and a low-pressure seal.

8. A catheter according to claim 7, wherein said high-pressure seal may be variably applied and released as desired.

9. A catheter according to claim 7, wherein said low pressure seal is a passive gasket.

10. A catheter according to claim 7, wherein said second fitting further comprises a port in fluid communication with said lumen of said second tubular member to allow the passage of fluid therethrough.

11. A method for removing air from a balloon catheter having a first tubular member having a lumen therein and distal and proximal portions; a second thin-filmed tubular member having a lumen therein and distal and proximal portions, wherein said second thin-filmed tubular member is coaxially disposed about said first tubular member; a balloon disposed at said distal end of said second thin-filmed tubular member and in fluid communication therewith; and a fitting having a high pressure seal, a low pressure seal and a port in fluid communication with said lumen of said second member, whereby said fitting is sealingly connected to said proximal portion of said second thin-filmed tubular member, and slidably mounted on said first tubular member; the method comprising the steps of:

loosening said high-pressure seal; sliding said fitting axially from said proximal portion of said first tubular member towards said distal portion of said first tubular member, thereby collapsing and contracting said second thin-filmed tubular member; coupling a syringe having a plunger and containing fluid to said port; and retracting said syringe plunger to draw air from said balloon and from said lumen of said second thin-filmed tubular member.

12. The method of claim 11, further comprising the step of sliding said fitting axially from said proximal portion of said first tubular member towards said distal portion of said first tubular member, until said second thin-filmed tubular member and said balloon are collapsed and contracted.

13. The method of claim 11, further comprising the step of maintaining said syringe in a plunger-up position to allow air to rise away from the tip of said syringe, and sliding said fitting toward said proximal portion of said first tubular member, thereby expanding said second thin-filmed tubular member and drawing the fluid from said syringe into said lumen of said second thin-filmed tubular member and into said balloon to provide inflation thereof.

14. The method of claim 11, further comprising the step of maintaining said syringe in a plunger-up position to allow the air to rise away from the tip of said syringe, and depressing said plunger of said syringe, thereby injecting said fluid into said lumen of said second thin-filmed tubular member, causing said fitting to slide toward the proximal portion of said first tubular member and filling said second thin-filmed tubular member.

15. The method of claim 11, further comprising the step of connecting a multi-position valve between said syringe and said port, wherein said valve is set to a first open position for drawing air into said syringe when said syringe plunger is retracted.

16. The method of claim 15, further comprising the step of setting said valve to a second closed position thereby blocking the fluid communication between said syringe and said port after said plunger is retracted and air is drawn into said syringe.

17. The method of claim 16, further comprising the step of disconnecting said syringe from said valve and connecting an inflation device containing inflation fluid to said valve to inflate said balloon.

18. The method of claim 17, further comprising the step of setting said valve to the first open position to allow fluid to be forced into said port.

19. The method of claim 18, further comprising the step of using said inflation device to inflate said balloon with said inflation fluid.

20. A balloon catheter comprising:
an elongate tubular member having a distal portion and a proximal portion and having a lumen extending longitudinally therein;
a balloon;
a flexible tubular member having a distal portion and a proximal portion, and having an inflation lumen extending longitudinally therein, said flexible tubular member disposed coaxially about said elongate tubular member, connected to and in fluid communication with said balloon, said distal portion of said flexible tubular member being attached to said distal portion of said elongate tubular member so that said lumen of said flexible tubular member is fluid-tight; and
a fitting connected to said proximal portion of said flexible tubular member and slidably mounted on said elongate tubular member, said flexible tubular member being adjustable in length along its longitudinal axis to allow said fitting to be positioned along said proximal portion and said distal portion of said elongate tubular member, said fitting having a port in fluid communication with said inflation lumen and said balloon to allow the passage of fluid therethrough.

21. A balloon catheter according to claim 20, wherein said fitting further comprises a high-pressure seal and a low-pressure seal.

22. A balloon catheter according to claim 20, wherein said flexible tubular member further comprises a thin-filmed membrane that may be collapsed in an accordion manner along its longitudinal axis when said fitting is slid towards the distal end of said elongate tubular member, thereby purging air contained within said flexible tubular member.

23. A balloon catheter according to claim 22, wherein said flexible tubular member and said balloon may be collapsed in an accordion manner when said fitting is slid towards the distal end of said elongate tubular member, thereby purging air contained within said flexible tubular member and said balloon.

24. A catheter comprising:
a first elongate member having a distal portion and a proximal portion with a first fitting;
a second tubular member having a distal portion and a proximal portion, and having a lumen therein, said second tubular member disposed coaxially about said first elongate member, said distal portion of said second tubular member being attached to said distal portion of said first elongate member so that said lumen is fluid-tight;
a second fitting connected to said proximal portion of said second tubular member and in fluid communication therewith, said second fitting slidably mounted on said first elongate member; and
said second tubular member being flexible such that said second tubular member is extendable along its longitudinal axis to allow said second fitting to be positioned along said proximal portion and said distal portion of said first elongate member.

25. A catheter according to claim 24, further comprising a balloon secured to said second tubular member, said balloon in fluid communication with said second tubular member and radially expandable in response to the fluid.

26. A catheter according to claim 24, wherein said first elongate member is comprised of a rigid material.

27. A catheter according to claim 24, wherein said second tubular member is comprised of a flexible thin-filmed membrane that may be collapsed in an accordion manner along its longitudinal axis.

28. A catheter according to claim 25, wherein said balloon and said second tubular member are comprised of a flexible thin-filmed membrane that may be collapsed in an accordion manner along their longitudinal axis.

29. A catheter according to claim 24, wherein said second fitting further comprises a high-pressure seal and a low-pressure seal.

30. A catheter according to claim 29, wherein said high-pressure seal may be variably applied and released as desired.

31. A catheter according to claim 29, wherein said low pressure seal is a passive gasket.

32. A catheter according to claim 29, wherein said second fitting further comprises a port in fluid communication with said lumen of said second tubular member to allow the passage of fluid therethrough.

33. A method for purging air from a dilatation catheter having an elongate tube defining an inflation lumen, comprising:
   a) collapsing said elongate tube along its longitudinal axis to reduce the volume that would be occupied by air;
   b) providing a port in communication with said inflation lumen to allow air to escape;
   c) coupling a syringe having a plunger to said port; and
   d) retracting said plunger to withdraw any remaining air from said inflation lumen.

34. The method of claim 33, further comprising the step of providing fluid in said syringe and maintaining said syringe in a plunger-up position to allow air to rise away from the tip of said syringe, expanding said elongate tube and thereby drawing the fluid from said syringe into said inflation lumen to provide inflation thereof.

35. The method of claim 33, further comprising the step of providing fluid in said syringe and maintaining said syringe in a plunger-up position to allow air to rise away from the tip of said syringe, then depressing said plunger of said syringe, thereby injecting the fluid into said inflation lumen and filling said elongate tube.

36. The method of claim 33, further comprising the step of connecting a multi-position valve between said syringe and said port, wherein said valve is set to a first open position for drawing air into said syringe when said syringe plunger is retracted.

37. The method of claim 36, further comprising the step of setting said valve to a second closed position thereby blocking the fluid communication between said syringe and said port after said plunger is retracted and air is drawn into said syringe.

38. The method of claim 37, further comprising the step of disconnecting said syringe from said valve and connecting an inflation device containing inflation fluid to said valve to inflate said elongate member.

39. The method of claim 38, further comprising the step of setting said valve to the first open position to allow fluid to be forced into said port.

40. The method of claim 39, further comprising the step of using said inflation device to inflate said balloon with said inflation fluid.

* * * * *